(12) United States Patent
Stookey et al.

(10) Patent No.: US 8,360,771 B2
(45) Date of Patent: Jan. 29, 2013

(54) HANDPIECE FOR DETECTION OF DENTAL DEMINERALIZATION

(75) Inventors: George K. Stookey, Carmel, IN (US); Charles L. Thomeczek, Jr., Fishers, IN (US); Jun Ge, Indianapolis, IN (US)

(73) Assignee: Therametric Technologies, Inc., Indianapolis, IN (US)

( * ) Notice: Subject to any disclaimer, the term of this patent is extended or adjusted under 35 U.S.C. 154(b) by 1204 days.

(21) Appl. No.: 11/617,103

(22) Filed: Dec. 28, 2006

(65) Prior Publication Data

US 2008/0160477 A1 Jul. 3, 2008

(51) Int. Cl.
*A61C 1/00* (2006.01)
*A61C 3/00* (2006.01)
(52) U.S. Cl. ........................................................ 433/29
(58) Field of Classification Search .............. 433/29–31; 600/179, 160, 109, 129, 175, 173, 189; 606/88–90
See application file for complete search history.

(56) References Cited

U.S. PATENT DOCUMENTS

| | | |
|---|---|---|
| 3,561,433 A | 2/1971 | Kovach |
| 4,279,594 A | 7/1981 | Rigutto |
| 4,290,433 A | 9/1981 | Alfano |
| 4,479,499 A | 10/1984 | Alfano |
| 4,515,476 A | 5/1985 | Ingmar |
| 4,976,951 A | 12/1990 | Rosenberg et al. |
| 5,061,880 A | 10/1991 | Hashiguchi et al. |
| 5,139,420 A | 8/1992 | Walker |
| 5,280,278 A | 1/1994 | Vick |
| 5,306,144 A | 4/1994 | Hibst et al. |
| 5,382,163 A | 1/1995 | Putnam |
| 5,449,290 A | 9/1995 | Reitz |
| 5,454,022 A | 9/1995 | Lee et al. |
| 5,503,559 A | 4/1996 | Vari |
| 5,550,380 A | 8/1996 | Sugawara et al. |
| 5,570,182 A | 10/1996 | Nathel et al. |
| 5,742,700 A | 4/1998 | Yoon et al. |
| 5,759,030 A | 6/1998 | Jung et al. |
| 5,818,587 A | 10/1998 | Devaraj et al. |
| 5,894,620 A | 4/1999 | Polaert et al. |
| 5,951,284 A | 9/1999 | Lake |
| 5,961,327 A | 10/1999 | Löhn |
| 6,008,889 A | 12/1999 | Zeng et al. |
| 6,024,562 A | 2/2000 | Hibst et al. |

(Continued)

FOREIGN PATENT DOCUMENTS

| | | |
|---|---|---|
| DE | 40 09 438 | 9/1991 |
| EP | 0 113 152 A2 | 7/1984 |
| EP | 0 326 497 A2 | 8/1989 |
| EP | 0 920 831 A1 | 6/1999 |
| EP | 1 269 909 A1 | 1/2003 |

(Continued)

OTHER PUBLICATIONS

Web pages (3), www.kavousa.com, DIAGNOdent, Kayo Diagno Dent, dated Mar. 10, 2001.

(Continued)

*Primary Examiner* — Todd Manahan
*Assistant Examiner* — Yogesh Patel
(74) *Attorney, Agent, or Firm* — Faegre Baker Daniels LLP

(57) ABSTRACT

A dental implement including a housing, a light source, and an air supply, the implement being suitable for examining tissue such as dentition of a patient and detecting loss of mineralization therein. The implement is capable of operating in a wireless mode. The implement is further able to communicate with a computing device to allow recording of images captured by the implement.

15 Claims, 9 Drawing Sheets

U.S. PATENT DOCUMENTS

| | | | |
|---|---|---|---|
| 6,053,731 | A | 4/2000 | Heckenberger |
| 6,074,616 | A | 6/2000 | Buechler et al. |
| 6,102,704 | A | 8/2000 | Eibofner et al. |
| 6,135,774 | A | 10/2000 | Hack et al. |
| 6,186,780 | B1 | 2/2001 | Hibst et al. |
| 6,231,338 | B1 | 5/2001 | de Josselin de Jong et al. |
| 6,276,934 | B1 * | 8/2001 | Rakocz ........................ 433/29 |
| 6,309,835 | B1 | 10/2001 | Iyer et al. |
| 6,393,315 | B1 | 5/2002 | Aprahamian et al. |
| 6,404,984 | B1 | 6/2002 | Parvulescu et al. |
| 6,443,729 | B1 | 9/2002 | Watson |
| 6,485,300 | B1 | 11/2002 | Muller et al. |
| 6,512,855 | B1 | 1/2003 | Delean |
| 6,522,147 | B1 | 2/2003 | Pickard et al. |
| 6,533,434 | B2 | 3/2003 | Yuen |
| 6,561,802 | B2 | 5/2003 | Alexander |
| 6,584,341 | B1 | 6/2003 | Mandelis et al. |
| 6,592,371 | B2 | 7/2003 | Durbin et al. |
| 6,672,868 | B1 | 1/2004 | Momot et al. |
| 6,724,522 | B2 | 4/2004 | Hartung |
| 6,761,561 | B2 | 7/2004 | Mandelkern et al. |
| 6,769,911 | B2 | 8/2004 | Buchalla et al. |
| 6,860,611 | B2 | 3/2005 | Gentz |
| 6,908,307 | B2 | 6/2005 | Schick |
| 6,958,766 | B2 | 10/2005 | Cooper |
| 6,964,567 | B2 | 11/2005 | Kerschbaumer et al. |
| 6,976,841 | B1 | 12/2005 | Osterwalder |
| 7,057,639 | B2 | 6/2006 | Spoonhower et al. |
| 7,070,412 | B2 | 7/2006 | Stadeker |
| 7,072,443 | B2 | 7/2006 | Schick et al. |
| 2003/0097122 | A1 | 5/2003 | Ganz et al. |
| 2003/0113823 | A1 | 6/2003 | Gregory |
| 2003/0122771 | A1 | 7/2003 | Sumiyoshi et al. |
| 2003/0148243 | A1 * | 8/2003 | Kerschbaumer et al. ........ 433/29 |
| 2003/0156788 | A1 | 8/2003 | Henning |
| 2003/0228553 | A1 * | 12/2003 | Mandelkern et al. .......... 433/29 |
| 2004/0023184 | A1 | 2/2004 | de Josselin de Jong et al. |
| 2004/0038169 | A1 | 2/2004 | Mandelkern et al. |
| 2004/0184643 | A1 | 9/2004 | Stantchev et al. |
| 2004/0202356 | A1 | 10/2004 | Stookey et al. |
| 2004/0236232 | A1 | 11/2004 | Jonusauskas et al. |
| 2004/0240716 | A1 | 12/2004 | de Josselin de Jong et al. |
| 2005/0003323 | A1 | 1/2005 | Katsuda et al. |
| 2006/0078844 | A1 * | 4/2006 | Goldman et al. ............... 433/80 |
| 2006/0188070 | A1 | 8/2006 | Razzano et al. |
| 2006/0199146 | A1 | 9/2006 | Mandelkern et al. |
| 2006/0204923 | A1 | 9/2006 | Stadeker |
| 2007/0134615 | A1 * | 6/2007 | Lovely ........................... 433/29 |
| 2007/0224571 | A1 * | 9/2007 | Watson .......................... 433/31 |

FOREIGN PATENT DOCUMENTS

| | | | |
|---|---|---|---|
| JP | 0 792 618 | A1 | 9/1997 |
| JP | 2004/089238 | A | 3/2004 |
| JP | 2004/163131 | A | 6/2004 |
| WO | WO 92/06671 | A1 | 4/1992 |
| WO | WO 96/12291 | A1 | 4/1996 |
| WO | WO 00/64242 | A1 | 11/2000 |
| WO | WO 00/67635 | | 11/2000 |
| WO | WO 01/02839 | A1 | 1/2001 |
| WO | WO 2004/089197 | | 10/2004 |

OTHER PUBLICATIONS

Brochure, "Sophistication. Simplified. The A-Dec Intraoral Camera", 2 pgs. (2003).

Brochure, "Introducing the Schick USBCam™ ", 2 pgs. (undated).

Alfano, et al., "Human Teeth With and Without Dental Caries Studied by Visible Luminescent Spectroscopy", J. Dent. Res., vol. 60, No. 2, pp. 120-122.

Al-Khateeb et al., "A Longitudinal Laser Fluorescence Study of White Spot Lesions in Orthodontic Patients," American Journal of Orthodontics and Dentofacial Orthopedics, vol. 113, No. 6, pp. 595-602 (Jun. 1998).

Al-Khateeb et al., "Light-Induced Fluorescence Studies on Dehydration of Incipient Enamel Lesions," Caries Research, vol. 36, pp. 25-30 (2002).

Al-Khateeb et al., "Light-Induced Fluorescence Studies on Dehydration of Incipient Enamel Lesions—Clinical Considerations," Caries Res., vol. 32, p. 285 (Abst #53) (1998).

Ando et al., "Comparative Study to Quantify Demineralized Enamel in Deciduous and Permanent Teeth Using Laser- and Light-Induced Fluorescence Techniques", Caries Res, vol. 35, pp. 464-470 (2001a).

Ando, et al., "Effect of Dehydration on White-Spot Quantification with QLF in Vitro", J. Dent. Res., vol. 80; p. 718 (Abst #1536) (2001b), 2 pgs.

Ando, et al., "Pattern of Fluorescence Intensity During Dehydration as Determined by Quantitative Light-Induced Fluorescence in Vitro", Caries Res., vol. 35, p. 270 (Abst #16) (2001c).

Angmar-Mansson, et al., "Quantitative Light-Induced Fluorescence (QLF): a method for assessment of incipient caries lesions", Dentomaxillofacial Radiology, No. 30, pp. 298-307 (2001).

Banerjee, et al., "Autofluorescence and Mineral Content of Carious Dentine: Scanning Optical and Backscattered Electron Microscopic Studies", Caries Research, vol. 32, pp. 219-226 (1998).

Banerjee, et al., "Dentine Caries Excavation: a review of current clinical techniques", British Dental J., vol. 188, No. 9 (May 13, 2000).

Banerjee, et al., "In vitro Evaluation of Five Alternative Methods of Carious Dentine Excavation", Caries Research vol. 34, pp. 144-150 (2000).

Fisher, et al., "Tooth-Caries Early Diagnosis and Mapping by Fourier Transform Spectral Imaging Fluorescence", Instrumentation Science & Technology, vol. 30(2), pp. 225-232 (2002).

Foreman, "Fluorescent Microstructure of Mineralized Dental Tissues", Intl. Endodontic Journal, vol. 21, pp. 251-256 (1988).

Fried, et al., "Infrared Spectroscopy of Laser Irradiated Dental Hard Tissues using the Advanced Light Source", Univ. California, San Francisco, Dept. of Preventive and Restorative Dental Sciences, 3 pgs. (undated).

Hefferren, et al., "Luminescence as a Tool to Study Enamel Interactions", Intl. Symposium on Tooth Enamel, pp. 161-165 (undated).

Mujat et al., "The Influence of Drying on Quantitative Laser Fluorescense and Optical Pathlengths in Incipient Natural Caries Lesions," Caries Research, vol. 38, pp. 484-492 (2004).

Pretty, et al., "Detection of in vitro demineralization of primary teeth using quantitative light-induced fluorescence (QLF)", Intl. Journal of Paediatric Dentistry, vol. 12, pp. 158-167 (2002).

Pretty et al., "The Effect of Dehydration on Quantitative Light-Induced Fluorescence Analysis of Early Enamel Demineralization," Journal of Oral Rehabilitation, vol. 31, pp. 179-184 (2004).

Shi et al., "Comparison of QLF and DIAGNOdent for Quantification of Smooth Surface Caries", Caries Research, No. 35, pp. 21-26 (2001).

Spitzer, et al., "The Total Luminescence of Bovine and Human Dental Enamel", Calcif. Tiss. Res., No. 20, pp. 201-208 (1976).

Stookey, "Optical Methods—Quantitative Light Fluorescence," Proceedings of International Consensus Workshop on Caries Clinical Trials, Jan. 6-10, 2002, Loch Lomund, Scotland, UK., J. Dent. Res., vol. 83(Spec Iss C) (2004).

Traneous, et al., "In vivo Repeatability and Reproducibility of the Quantitative Light-Induced Fluorescence Method", Caries Research No. 36, pp. 3-9 (2002).

Van Der Veen, et al., "Caries Activity Detection by Dehydration with Quantitative Light Fluorescence", report of Indiana Conference 1999 Early Detection of Dental Caries II, pp. 251-259 (1999).

Van Der Veen, et al., "The Influence of Mineral Loss on the Auto-Fluorescent Behavior of in vitro Demineralised Dentine", Caries Research, vol. 30, pp. 93-99 (1996).

Angmar-Månsson et al., "Optical methods for the detection and quantification of caries," Adv. Dent. Res. 1987; 1:14-20.

Ando et al., "Evaluation of the Effect of Dehydration on Demineralized Enamel with Quantitative Light-Induced Fluorescence (QLF)," Caries Res. 2000; 34(4): 326 (Abst. 52), 2 pgs.

Van Der Veen et al., "Caries activity detection by dehydration with QLF," Caries Res. 2000; 34: (Abstract #53) 326.

Mujat et al., "The influence of drying on QLF and Optical Pathlengths in incipient natural caries lesions in vitro," Caries Res 2002; 36:191 (Abstract #53).

Doi et al., "The effect of dehydration on dental autofluorescence for white-spot lesions and natural developmental defects," Caries Res 2005; 39: 302 (Abstract # 44).

\* cited by examiner

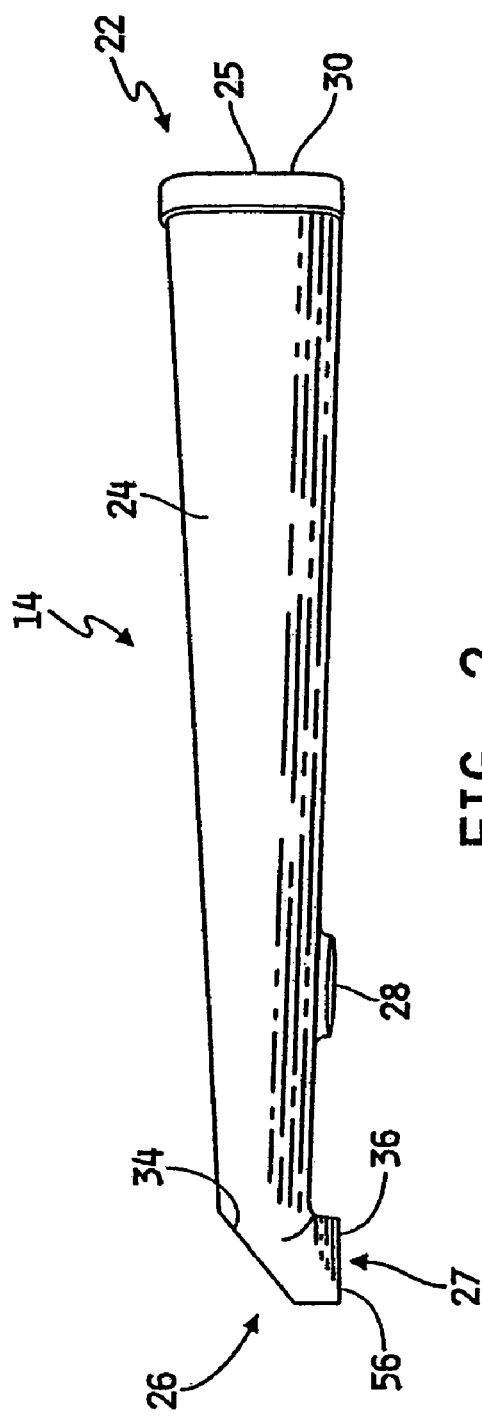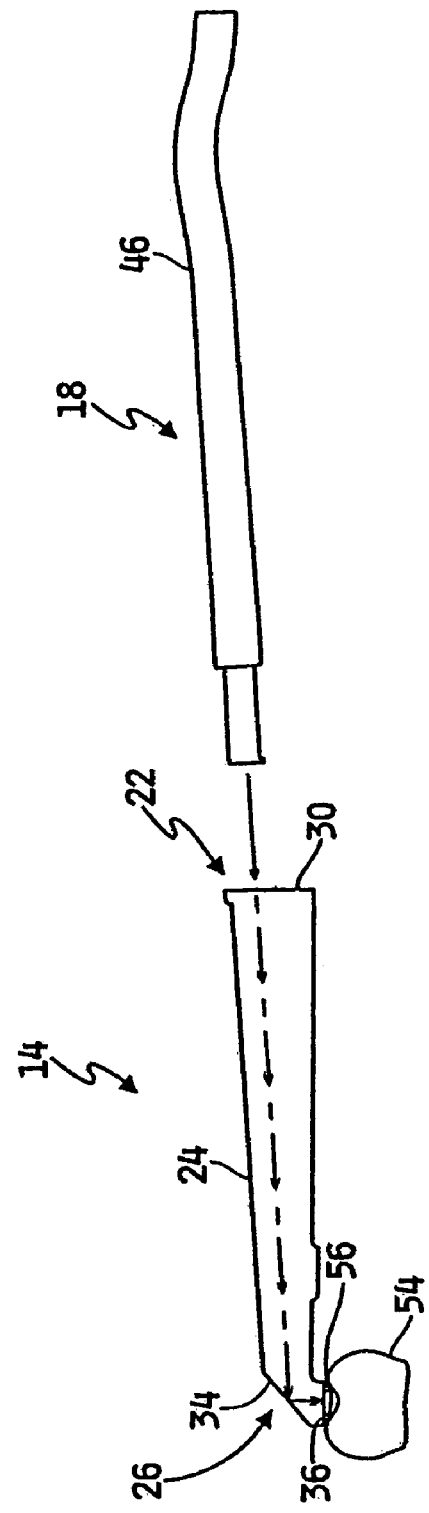

HANDPIECE FOR DETECTION OF DENTAL DEMINERALIZATION

BACKGROUND AND SUMMARY

The invention relates to dental devices and more particularly to devices for detection of tooth decay/dental demineralization.

While there has been a remarkable decline in the prevalence of dental caries (tooth decay) in U.S. children and adults during the past 40 years, dental caries continues to be a major public health problem in select portions of the U.S. population. Dental caries has been identified as the single most common chronic disease of childhood. Despite the strides made in treating and preventing dental caries, significantly more needs to be done to further combat the problem.

Dental caries is a chronic infectious disease and earlier detection would reduce the ravages of the disease. Current caries detection methods (clinical exams, x-rays) are unable to detect the decay process until it has progressed to a point where it is necessary to place a restoration (filling). Since the loss of mineral (demineralization) from the enamel is a chronic process that occurs over a period of months to years, and since very small lesions (i.e., early detection) are completely reversible through the use of fluoride treatments and other preventive measures, the early detection of dental demineralization allows dental professionals to administer professional treatments to reverse the demineralization process rather than undertake more costly and less desirable restorative treatments.

According to one embodiment of the present disclosure, a handheld dental implement is provided. The implement includes a housing defining an interior space; a power source; a light source electrically coupled to the power source; and a gas reservoir.

According to another embodiment of the present disclosure, a wireless handheld dental implement is provided. The implement includes a housing defining an interior space; a power source; a light source electrically coupled to the power source; a reflective surface; and a gas conduit positioned to transmit gas into contact with the reflective surface.

According to still another embodiment of the present disclosure, a handheld dental implement is provided. The implement includes a power source; a light source electrically coupled to the power source; and a microphone.

According to yet another embodiment of the present disclosure, a dental investigation system is provided. The system includes a handpiece including a light source, a light detecting device, and a wireless communicator; and a receiver coupled to a processing unit configured to receive wireless transmissions from the handpiece.

According to another embodiment of the present disclosure, a dental investigation system is provided. The system includes a processing unit; a handpiece in communication with the processing unit; and a microphone in communication with the processing unit.

According to still another embodiment of the present disclosure, a method of recording data regarding a dental subject is provided. The method includes the steps of receiving pictures of a dental subject; associating the pictures with the dental subject; receiving audio input, the audio input containing information related to the dental subject; and associating the audio input with the dental subject.

According to another embodiment of the present disclosure, a computer readable medium is provided. The computer readable medium includes instructions thereon such that when interpreted by a processor cause the processor to perform the steps of receiving pictures of a dental subject; associating the pictures with the dental subject; receiving audio input, the audio input containing information related to the dental subject; and associating the audio input with the dental subject.

Additional features of the invention will become apparent to those skilled in the art upon consideration of the following detailed description of the illustrated embodiment exemplifying the best mode of carrying out the invention as presently perceived.

BRIEF DESCRIPTION OF THE DRAWINGS

The detailed description particularly refers to the accompanying figures in which:

FIG. 2 is a perspective view of a lightpipe of the handpiece of FIG. 1;

FIG. 3 is a cross sectional view of a light source and the lightpipe of FIG. 1 in contact with a tooth of a patient;

DETAILED DESCRIPTION OF THE DRAWINGS

Tooth decay or dental caries result from a de-mineralization of dental tissue. Introduction of light to dental tissue and observance of the fluorescence of the dental tissue allows early detection of dental demineralization through a process called quantitative light fluorescence (QLF). "QLF" has been trademarked by Inspektor Dental Care (hereinafter "Inspektor"). The use of the term "QLF" herein is meant to denote a quantitative light fluorescence type system, and not the specific system of Inspektor unless specifically stated otherwise. QLF allows earlier detection than a purely visual inspection and does not have the side effects associated with radiographic examinations. Furthermore, QLF provides an objective method of analysis of dental demineralization by permitting a dentist or other caregiver to quantify the size of lesions as well as monitor changes in the size of lesions over time. A more detailed description of QLF and a method for utilizing QLF is described in U.S. patent application Ser. No. 10/411,625 to Stookey et al. filed Apr. 10, 2003, the disclosure of which is incorporated herein by reference. Generally speaking, green fluorescence is analyzed to determine demineralization and red fluorescence is analyzed to determine the presence of plaque.

Figure 1:
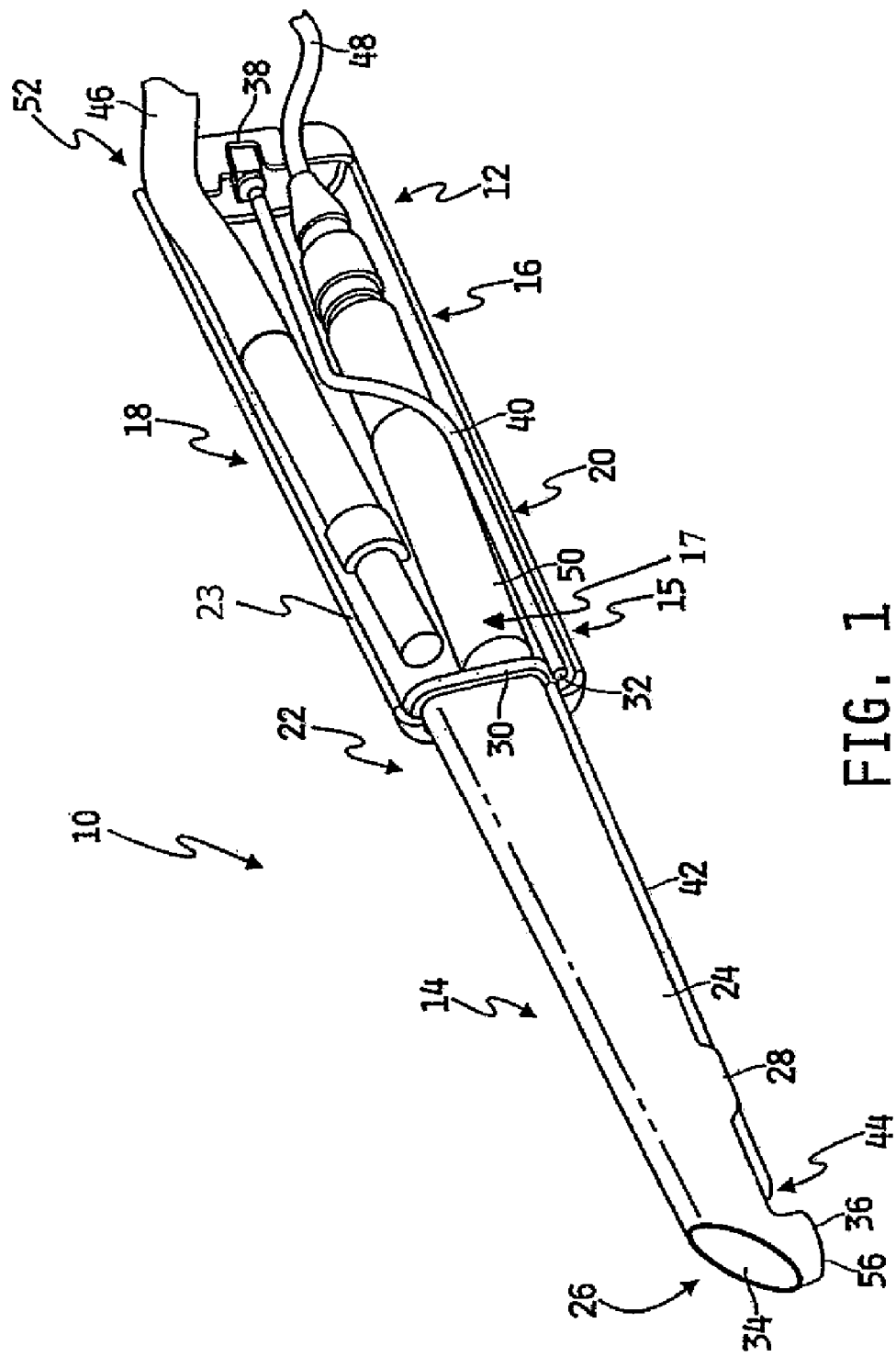
FIG. 1 is a perspective, partially cut-away view of a handpiece for detection of dental demineralization.

To gather data for processing in a QLF system, a handpiece 10, shown in FIG. 1, is utilized. Handpiece 10 includes a handle or shell 12, a light pipe 14 attached to shell 12, an optical train 15 to receive light from light pipe 14, a camera 16 to detect light provided to optical train 15, a light source 18 to provide light to light pipe 14, and a conduit 20 extending through shell 12. Shell 12 includes a left half shell (not shown) and a right half shell 23 that cooperate to house, at least partially, optical train 15, camera 16, light source 18, and conduit 20. Shell 12 furthermore couples to light pipe 14 as shown in FIG. 1.

Shell 12 includes inner cavities shaped to receive and hold camera 16, light source 18, inter-shell hose 40, and light pipe 14 in specific orientations. Lip 30 of light pipe 14 is received in recess 32 of shell 12. Likewise, light source 18 is positioned to allow light therefrom to be directed through light pipe 14, off reflecting facet 34, and out inspection surface 36. Similarly, camera 16 is positioned such that light entering inspection surface 36, reflecting off reflecting facet 34, and traveling through light pipe 14 is received by camera 16. Additionally, shell 12 provides for wires (fiber optic, electrical, or otherwise) to extend from a rear end 52 thereof. A fiber optic cable 46 extends to the external light source (not shown), an electrical cable 48 extends to a computer 1126 to store, process, and display the image received by camera 16.

Light source 18 is preferably a fiber optic system that conveys illumination from a remote source but may also be a local source within shell 12 or any other source known in the art. The light may be optically filtered by the system either before or after exiting light source 18. Such filtering excludes unwanted light and noise from the desired signal. Furthermore, in one embodiment, light source 18 includes one or more light emitting diodes, laser diodes, or some combination thereof (locally or remotely). In such embodiments, each of the light sources may be of a different wavelength and combined as desired. The wavelength of the light used may be tailored, lengthened or shortened, to the dental tissue being observed as well as to the desired light penetration and to the light collection instrumentation (camera 16) so as to provide the desired optical response. It should be appreciated that while much of the description herein refers to fluorescence as the desired optical response, all types of optical responses are intended to within the scope of the present disclosure. It should also be appreciated that the term "dental tissue" is used herein to include all types of tissue found in the mouth, i.e. teeth, gums, tongue, cancerous cells.

Optical train 15 includes a lens 50 and at least one filter. Embodiments are envisioned where lens 50 and the filter(s) may be combined into one structure or where no filter is present. Optical train 15 tailors the incoming information into a form that is best received by camera 16 and that best provides the data for processing. Such tailoring may include providing selective attenuation of the reflected or scattered input illumination, in addition to fluorescent emission data. While optical train 15 is described as having one lens 50 and filter, many lenses and filters may be included in optical train 15 to provide different fields of view and different magnifications.

Camera 16 is part of a digital imaging system that collects high-resolution images and live video of dental tissue. Camera 16 then transmits the images, either through a wire as shown or wirelessly, to computer 1126 for storage and processing. When describing handpiece 1010 as "wireless," it should be appreciated that 'wireless' is intended to refer to the lack of electrical or supply lines extending to or from handpiece 1010 that would tether handpiece 1010 to another object such as a computer 1126 or an air supply (not shown). One suitable model camera is the DXC-LS1/1 sold by Sony. In the present embodiment, camera 16 is a color camera that detects spectral responses of tissue to the provided illumination. However, in another embodiment, camera 16 is a black and white sensing camera. In one embodiment using black and white camera 16, a bandpass filter 17 as part of optical train 15 configured to filter out light of substantially the same wavelength as the illumination source 18 is used and black and white camera 16 is used to detect scattering intensity. In another embodiment using black and white camera 16, a bandpass filter 17 configured to filter out light of substantially the same wavelength as the tissue fluorescence is used and black and white camera 16 detects the intensity of tissue fluorescence.

Before reaching camera 16, the light of the tooth images passes through light pipe 14. Light pipe 14 is a translucent (transparent) monolithic polymer such as polystyrene, polycarbonate, acrylic, or glass piece that attaches to an end of the shell 12. "Translucent" as used herein is meant to describe any material that is not opaque, thus meaning anything that transmits light while causing light diffusion as well as anything that is transparent (transmitting light without causing substantial light diffusion). While light pipe 14 is described and shown as being a solid piece, embodiments are envisioned having voids and gaps within light pipe 14. Light pipe 14 is constructed from polycarbonate but may be constructed from any material that will allow light transmission of an adequate fidelity and acceptable, preferably low, signal loss.

As shown in FIG. 2, light pipe 14 includes a proximal attachment end 22, a tapering body 24, a distal end 26, and a conduit support 28. Proximal attachment end 22 includes a lip 30 of constant depth and width. Lip 30 is sized and shaped to be securely received in a recess 32 of shell 12. Separating left half shell (not shown) from right half shell 23 allows removal of light pipe 14. Coupling left half shell (not shown) to right half shell 23 secures light pipe 14 to shells 21, 23. Alternatively, shell 12 may be configured to have a pocket that slidably receives lip 30 therein and is secured by a latch so as to not require the detachment of left half shell (shown) from right half shell 23.

Figure 4:
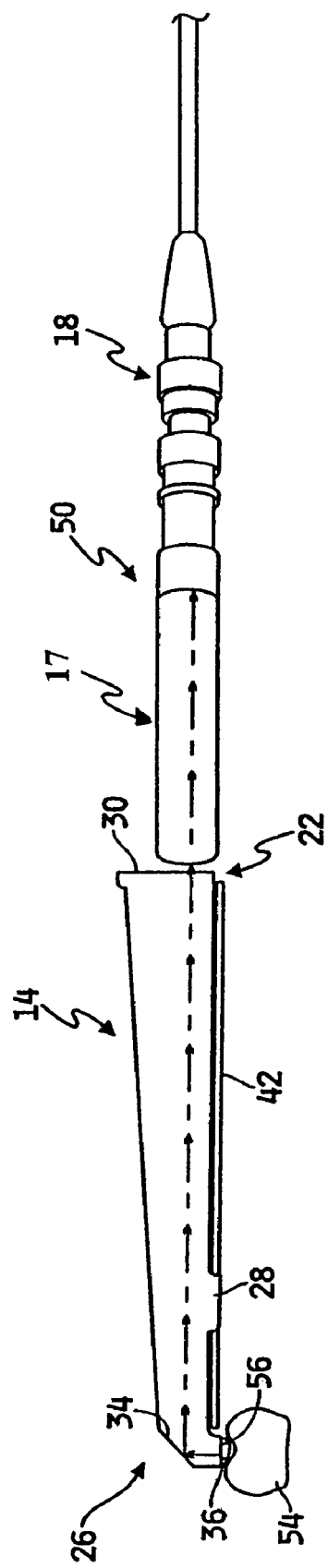
FIG. 4 is a side elevational view of a camera and the lightpipe of FIG. 1 in contact with a tooth of a patient.

Tapering body 24 includes conduit support 28 attached thereto which will be discussed in more detail below. Distal end 26 includes a reflecting facet 34 and an inspection surface 36. Reflecting facet 34 is in internal surface of light pipe 14. Reflecting facet 34 allows light entering from proximal attachment end 22 across a proximal light transfer plane 25 to reflect and exit through distal light transfer plane 27 of inspection surface 36 as shown in FIG. 3. Likewise, reflecting facet 34 allows light entering from distal light transfer plane 27 of inspection surface 36 to reflect and exit through proximal light transfer plane 25 of proximal attachment end 22 as shown in FIG. 4. As will be discussed in more detail later, reflecting facet 34 is shaped even more specifically to direct light from inspection surface 36 to camera 16. The reflective properties of reflecting facet 34 are provided by the difference in refractive index between the material of light pipe 14 and the air surrounding light pipe 14. Thus, it is not necessary to attach a reflective surface to light pipe 14 to achieve the reflecting properties of reflecting facet 34. However, embodiments are envisioned where an external member is attached to light pipe 14 to provide reflective properties.

Reflecting facet 34 is preferably at a 45-degree angle relative to inspection surface 36 and proximal attachment end 22. The 45-degree angle allows true image transmission and refraction between inspection surface 36 and proximal attachment end 22. However, it should be appreciated that embodiments are envisioned where reflecting facet 34 is not at a 45-degree angle, and various lenses, optical filters, and/or optical processors, either integral or external to light pipe 14, are utilized to construct a true image.

Tapering body 24 and distal end 26 are sized and shaped to be received in the mouth of a patient and to access posterior molars which, as a function of being farthest from the mouth opening, are typically the most difficult to access. Additionally, the size and shape of tapering body 24 allows the device to be used on smaller patients where oral space is more limited. Furthermore, light pipe 14 is lightweight, and as such provides increased maneuverability and less user fatigue.

Conduit 20 is provided to selectively deliver air to tooth 54 to dehydrate suspected lesions. Alternatively, conduit 20 may delivery any number of fluids to a position proximate distal end 26 of light pipe 14 such as a fluoride containing solution, other reparative fluids, a contrast agent, or a biomarker.

Conduit 20 extends within shell 12 and below tapering body 24. As shown in FIG. 1, conduit 20 includes a connector 38, an inter-shell hose 40, and an extra-shell channel 42. Connector 38 allows an external supply hose (not shown) to supply air, water, or another fluid to be attached to inter-shell hose 40. Inter-shell hose 40 is coupled to extra-shell channel 42 via shell 12 to allow matter from inter-shell hose 40 to pass into extra-shell channel 42 and out a distal end 44 of extra-shell channel 42. Extra-shell channel 42 is a metal channel that couples to conduit support 28 of light pipe 14 for support. Distal end 44 of extra-shell channel 42 is positioned such that any matter exiting therefrom will be proximate inspection surface 36. Such local delivery assists a caregiver in determining the activity status of a detected lesion.

To effect the delivery, a supply tube of air (not pictured) is attached to connector 38 and air is selectively pumped therethrough. Connector 38 is coupled to inter-shell hose 40 which is coupled to extra-shell channel 42 to allow localized delivery of the desired material. Furthermore, while the extra-shell channel 42 is shown as a tube that removably couples to an underside of light pipe 14, other embodiments include extra shell channel 42 defined within light pipe 14.

The shape and makeup of light pipe 14 are designed to create a focal plane 56 for camera 16 at or proximate to inspection surface 36. In use, inspection surface 36 is placed within a patient's mouth to abut a selected tooth 54. Abutting selected tooth 54, combined with the location of focal plane 56 of camera 16 allows for a caregiver to easily find a location for handpiece 10 resulting in a clear picture. Focal plane 56 is configured to be at a distance that is the sum of the horizontal and vertical distances shown by dotted line in FIG. 4. Abutting inspection surface 36 with tooth 54 results in reproducibility of the desired picture from one inspection to the next by removing possible fluctuation of the distance between inspection surface 36 and tooth 54 between successive inspections and by reducing fluctuations from unsteadiness of an operator's hand. Light from light source 18, as it travels to and from tooth 54, only passes through ambient air for a short distance, if at all, when the inspection surface 36 abuts tooth 54. Control over the mediums through which the light passes increases the amount of control present over the signal and reduces chances for error that may be introduced if foreign matter is allowed in the light path. Furthermore, inspection surface 36 abutting tooth 54 increases the likelihood that only light provided by light source 18 is exciting the observed dental tissue and that the fluorescence observed by camera 16 is a result of the provided illumination rather than from ambient light. Inspection surface 36 abutting tooth 54 covers the portion of tooth 54 to be examined by the caregiver, thus light pipe 14 simultaneously provides desired illumination while not providing space between tooth 54 and handpiece 10 that would allow undesired tooth illumination.

It should also be appreciated that acrylic light pipe 14, or any plastic equivalent created by injection molding or otherwise, is relatively inexpensive to manufacture and thus may be used in a disposable fashion. Such disposable use results in increased hygiene practices for a dental practitioner. Non-disposable dental implements are typically subjected to a sterilization process, such as autoclaving, between patients. This sterilization is costly and can cause deterioration of the material being sterilized. Deterioration of a light pathway such as a lens, a mirror/reflecting surface, or a translucent material can adversely effect the pictures gathered from such equipment. Accordingly, the disposable nature of light pipe 14 results in increased image fidelity and increased hygiene for the patient. However, embodiments are also envisioned that incorporate a reusable light pipe 14.

Another embodiment handpiece 1010 is shown in FIGS. 6-10. Handpiece 1010 includes many similar pieces to those shown in handpiece 10. Handpiece 1010 includes shell 1012, and end cap 1014 selectively attached to shell 1012. Shell 1012 houses lens 1013, prism 1015, camera 1016, filter 1017, LED's 1018, air outlet conduit 1020, air valve 1060 coupled to air outlet conduit 1020, air outlet valve button 1062, air supply valve 1064, air canister 1066, battery 1068, electronics 1070, and on/capture button 1072. End cap 1014 includes left end cap housing 1080, right end cap housing 1082, and mirror 1084.

Shell 1012 is composed from plastic, includes right shell housing 1086, and left shell housing 1088. Right and left shell housings 1086, 1088 each include button hole 1090 and power lead hole 1092. When assembled, right and left shell housings 1086, 1088 form a closed proximal end 1094 and an open distal end 1096. Open distal end 1096 includes an exterior groove therein that cooperates with an inner surface (not shown) of end cap 1014 to provide a keyed interlock therebetween. Each button hole 1090 is sized shaped, and located to receive and allow external exposure of one of capture button 1072 and air outlet valve button 1062. Each power lead hole 1092 is sized, shaped, and located to receive and allow external exposure of electrical leads 1098 of battery 1068.

Lens 1013, prism 1015, and filter 1017 function similarly to optical train 15 to condition light to be received by camera 1016. LED's 1018 emit light that reflects off mirror 1084 and illuminates tooth 54. In the current embodiment, LED's 1018 emit light having a wavelength of 405 nm.

Air canister 1066 includes outlet hub 1100 that couples to hub 1102 of air supply valve 1064. Air supply valve 1064 further includes air inlet 1104 and air output 1106 coupled to air valve 1060. Air valve 1060 is operated via air outlet valve button 1062. Depression of air outlet valve button 1062 opens air valve 1060 and allows fluid communication between air canister 1066 and air outlet conduit 1020. Air outlet conduit 1020 fluidly couples to cap conduit 1108 when end cap 1014 is coupled to shell 1012. Air inlet 1104 is configured to receive an air supply hose (not shown) therein to provide an air charge to air canister 1066. Accordingly, air canister 1066 may be recharged as desired. Once charged, air canister 1066 provides pressurized air in air supply valve 1064 and air valve 1060. Thus, depression of air outlet valve button 1062 allows the pressurized air to escape via air outlet conduit 1020 and cap conduit 1108. Valve 1060 may be electrically or mechanically operated and air outlet valve button 1062 may be an electrical or mechanical button. Depression of air outlet valve button 1062 allows valve 1060 to open for a pre-determined length of time. Alternatively, valve 1060 is opened as long as air outlet valve button 1062 is depressed.

Camera 1016 is coupled to and controlled by electronics 1070 and powered by battery 1068. Capture button 1072 provides an input to electronics 1070 to operate camera 1016. Electronics 1070 include antenna 1071 that allows wireless transmission of images from camera 1016. Antenna 1071 may be embedded in electronics 1070 or physically separate therefrom. As previously noted, battery 1068 includes exposed electrical leads 1098 that allow battery 1068 to be re-charged. One embodiment includes microphone 1099 coupled to electronics 1070. Operation of microphone 1099 is discussed in more detail below. Embodiments are also envisioned where microphone 1099 is located outside of handpiece 1010. Such embodiments include having microphone 1099 positioned generally within the room of an examination and electronically coupled, wired or wirelessly, to computer 1126.

End cap 1014 selectively attaches to shell 1012 and includes excitation/air window 1110 and cap conduit 1108. End cap 1014 is designed to be disposable such that many disposable end caps 1014 would be used with each shell 1012 and its contents over the lifetime of handpiece 1010. Mirror 1084 is oriented at a 45 degree angle relative to LED's 1018, filter 1017, and near surface 1112 of camera 1016 to direct light from tooth 54 to camera 1016 and from LED's 1018 to tooth 54. Cap conduit 1108 is located such that air exiting therefrom creates a current along mirror 1084 and tooth 54.

Figure 11:
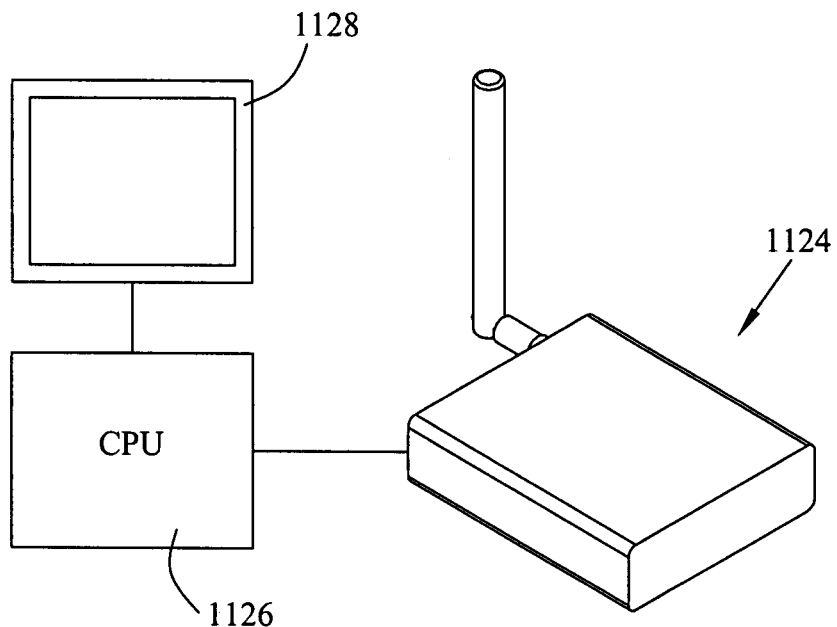
FIG. 11 is a diagrammatical view of a computer and receiver for use with the handpiece of FIG. 6.

FIG. 11 shows handpiece 1010 in a cradle 1114. Cradle 1114 includes housing 1116, power cord 1118, and internal electrical contacts (not shown). Housing 1116 includes bay 1122 that is sized to at least partially receive closed proximal end 1094 therein. Power cord 1118 is electrically coupled to the internal electrical contacts, potentially via a transformer (not shown). The internal electrical contacts are located within bay 1122 such that the internal electrical contacts abut electrical leads 1098 when handpiece 1010 is placed within cradle 1114. Bay 1122 may include a longitudinal keyway (not shown) therein that receives a key (not shown) disposed along or on shell 1012 of handpiece 1010 to align electrical leads 1098 with the internal electrical contacts. Cradle 1114 may also include a lever system (not shown) coupled to an air supply (not shown) such that placement of handpiece 1010 within cradle 1114 causes automatic charging of air canister 1066. Alternatively, air canister 1066 may be charged in cradle 1114 in a non-automatic manner or by manual connection of an air source (not shown) to air inlet 1104 when handpiece 1010 is out of cradle 1114.

FIG. 11 shows wireless receiver 1124. Wireless receiver 1124 couples to a computer 1126, via a wired connection, to allow wireless communication between computer 1126 and handpiece 1010. The wireless communication may include a video signal or still pictures from camera 1016 and audio signals from microphone 1099.

When examining teeth, active (growing) lesions, inactive lesions, and developmental defects are characterized by a localized decrease in mineralization, or demineralization. Defects are not typically repairable and inactive lesions often remain in such a state for years with no worsening of the condition. However, active lesions are growing decay that provide a heightened risk to the patient. Therefore, it is desirable to discriminate an active lesion from an inactive lesion or a tooth defect.

Blowing air on the surface of tooth 54 containing the suspected lesion allows dehydration of the lesion and results in a change in the fluorescence of tooth 54 when properly illuminated if the lesion is active. Non-active lesions and defects show little or no change in damage when dehydrated. Thus, it is desirable to be able to dehydrate lesions once found to determine their nature. It is furthermore desirable to be able to introduce a dehydration agent without gross alteration of camera 16 or the picture being taken so as to allow easy comparison of the hydrated and dehydrated pictures of the lesion.

In use, a dental care provider selects handpiece 10 and attaches lightpipe 14 (disposable or otherwise) thereto. Then, in certain embodiments, the provider places handpiece 10 within a sanitary sheath (not pictured) preferably made of thin plastic to provide a contaminant barrier for the entire handpiece 10. With or without the sheath, extra-shell channel 42 is coupled to lightpipe 14 and intra-shell hose 40. The external light source (not shown) and computer 1126 are activated to provide light to light source 18 and to receive data from camera 16. The provider then places distal end 26 of lightpipe 14 into the mouth of the patient such that inspection surface 36 of lightpipe 14 abuts chosen tooth 54.

Alternatively, a dental care provider selects handpiece 1010 and attaches end cap 1014 to shell 1012. End cap 1014 includes cap conduit 1108 integrally therein, so an external conduit, such as extra-shell channel 42, is not necessary. Computer 1126 and wireless receiver 1124 are activated to receive data from camera 1016 and microphone 1099. The provider then places end cap 1014 portion of handpiece 1010 into the mouth of the patient such that air window 1110 of end cap 1014 abuts chosen tooth 54.

If the patient has been examined with the system before, using either handpiece 10 or handpiece 1010, then, for each examined tooth 54, computer 1126 is instructed to access the past images of the tooth 54 (hereinafter, the "past images"). The provider, using computer 1126, attempts to match the placement of inspection surface 36 to the placement used for the past images. The matching process may take the form of an overlay of the current video signal with the past image of tooth 54 shown on monitor 1128 of computer 1126. Such an overlay may provide an indication of the alikeness of individual pixels such that a dental professional may visually interpret the number of alike pixels. The dental professional then adjusts the handpiece 10, 1010 to achieve what appears to be a maximum number of alike pixels.

It should be appreciated that abutting of inspection surface 36 (or end cap 1014 proximate air window 1110) to tooth 54 removes one direction of motion that must be re-aligned to the previous examination. Once the dental professional achieves what he believes is the optimal position, the dental professional presses capture button 1072 or otherwise causes the picture to be recorded (hereinafter, the "first picture"). The provider then continues to perform this procedure on each tooth 54.

If, at any point, a suspected lesion is found, the first picture of tooth 54 is taken just as for any other tooth. Then, at some later time during the visit, air is introduced via depression of a foot pedal (not shown), depression of air outlet valve button 1062, or otherwise sent through conduit 20 and cap conduit 1108 to dehydrate the lesion. The lesion is then checked for activity. One manner of determining the activity status of a suspected area involves taking a second picture of tooth 54 after the air is introduced to the tooth. After the introduction of air, the dental professional again attempts to match the placement of the handpiece 10, 1010 to the position used for taking the first picture. Once the positioning is sufficiently alike, capture button 1072 is depressed or the handpiece 10, 1010 is otherwise instructed to record an image. Computer 1126 then performs the overlay or other comparison of the second picture to the first picture. Computer 1126 determines the change in fluorescence, expressed as a percent change in fluorescence in one embodiment. If the fluorescence has changed between the two pictures by a pre-defined percentage, then the lesion is known to be active. However, if the fluorescence has not changed by the pre-defined percentage, then the lesion is held to be inactive or held to be a tooth imperfection. Embodiments are envisioned where the finding of an active lesion is accompanied by a beep sound or other obvious sound or visual indicator. Likewise, the finding of a non-active lesion is accompanied by an indicator that is easily distinguishable from the indication of an active lesion.

A finding of an active lesion permits the dental professional to implement a preventive treatment regimen consisting of periodic professional applications of a fluoride system, e.g., a fluoride varnish, and home-use of a daily fluoride treatment regimen. After a period of 2-3 months the lesion may be re-examined to determine the status and the need for further treatment regimens.

During the examination the dental professional may wish to provide information, record notes regarding the patient, or to orally provide instruction regarding handpiece 1010 operation. Accordingly, microphone 1099 is provided. Microphone 1099 is in communication with voice-recognition software on computer 1126 via antenna 1071 and wireless receiver 1124. The dental professional may indicate which tooth 54 is currently being investigated or shown via pictures from camera 1016 as well as indicating which surface of tooth 54 is being investigated/shown. Accordingly, pictures and audio information regarding tooth 54 are associated with tooth 54 at computer 1126. Patient notes may include the status of found lesions, periodontal conditions, or any other information that would be useful when reviewing the pictures. Additionally, microphone 1099 may be used to cause action within computer 1126 or handpiece 1010. Microphone 1099 may be used to cause action within computer 1126 by audibly declaring which tooth 54 is being observed. Whereas the software may include a system that stores one or more pictures for each tooth 54, the audible declaration by the dental professional may be used to indicate to computer 1126 which tooth 54 is about to be viewed for purposes of bringing up the past image of tooth 54. Similarly, the audible declaration instructs the software to save any taken first images so as to associate them with the proper tooth 54. Microphone 1099 may also be used to cause action within handpiece 1010 or computer 1126. Upon achieving desired placement of handpiece 1010, the dental professional may utter, "capture" or other chosen language to instruct handpiece 1010 or the software in computer 1126 to save an image. Other events, such as turning handpiece 1010 on and off may also be set up to be performed in response to verbal commands. Using verbal commands instead of a physical activity, such as depressing capture button 1072 may increase image surety by lessening the likelihood that handpiece 1010 will be moved and the taken image changed by the dental professional moving to depress capture button 1072. Other embodiments are envisioned where microphone 1099 is not part of handpiece 1010 but is rather otherwise coupled to the computer 1126.

Figure 5:
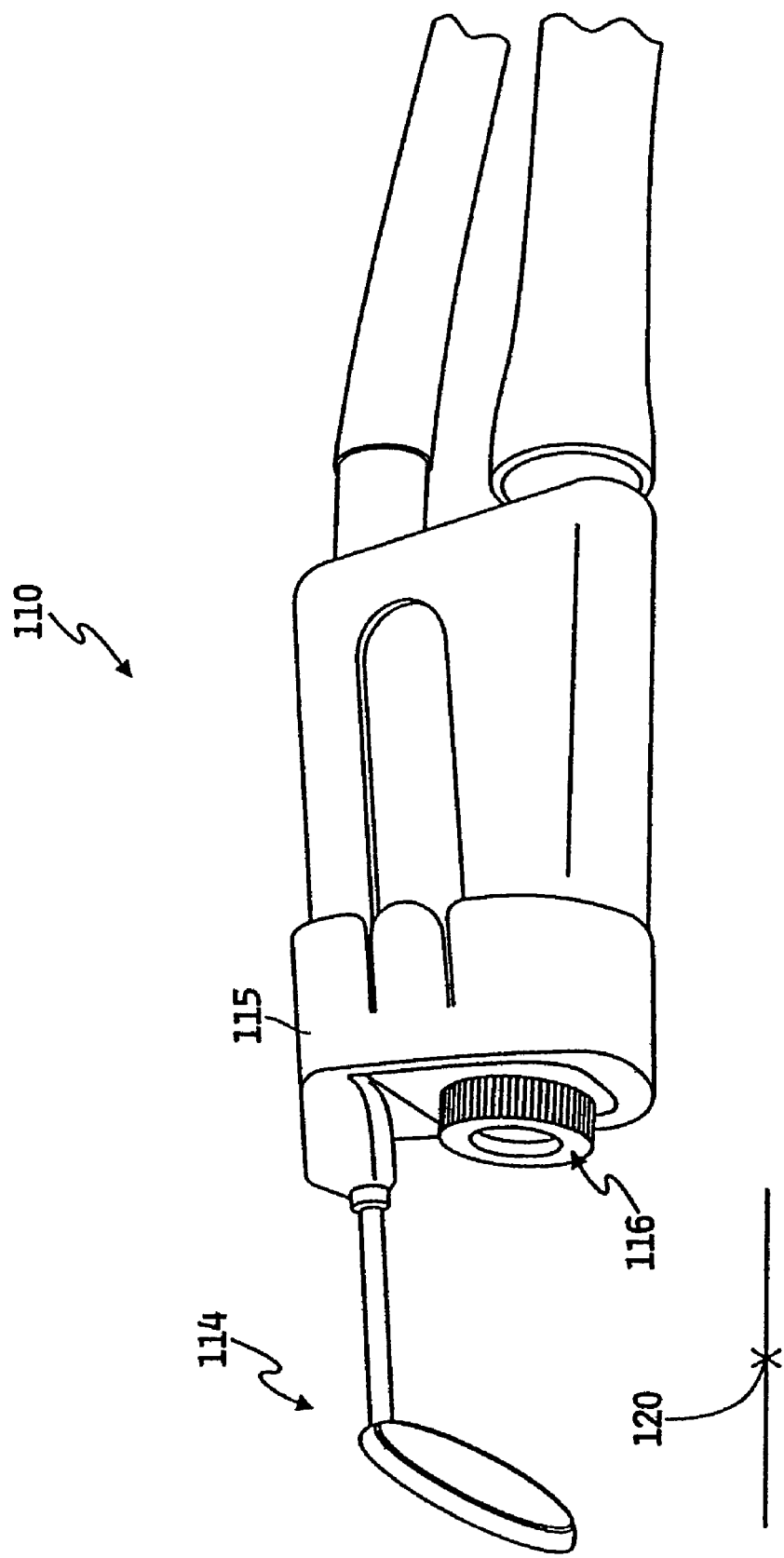
FIG. 5 is a perspective view of a prior art handpiece.
Figure 6:
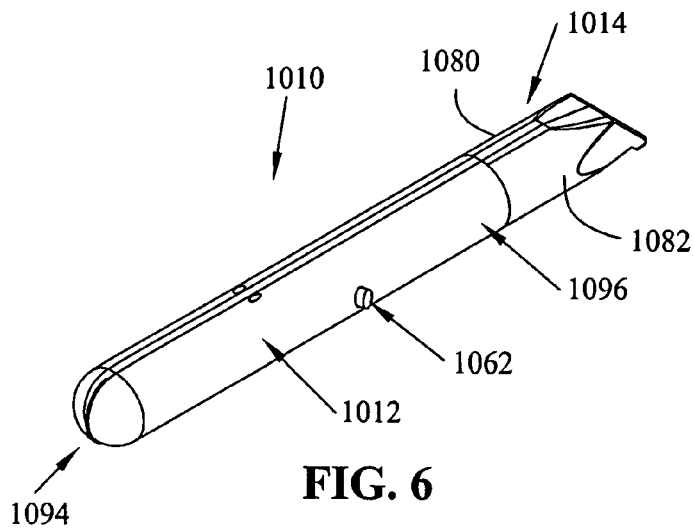
FIG. 6 is a perspective view of a second embodiment handpiece for detection of dental demineralization.
Figure 7:
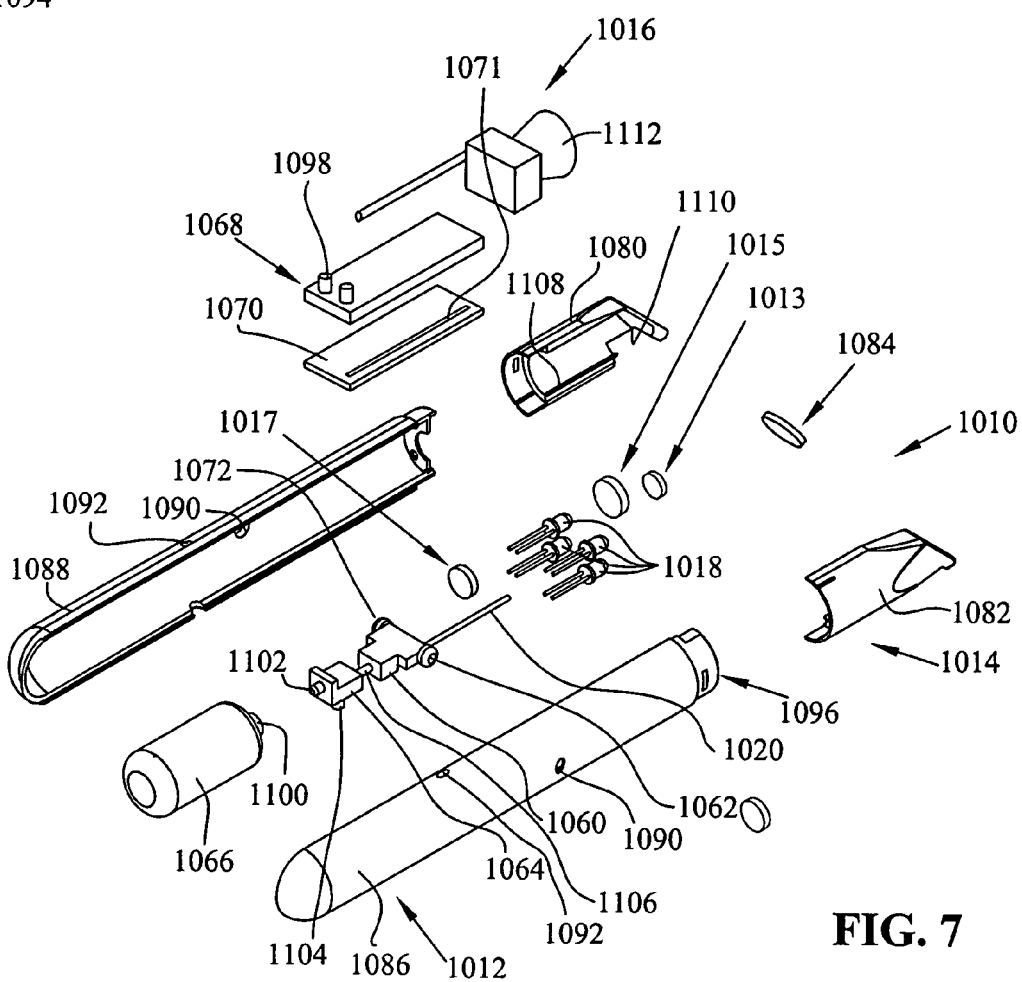
FIG. 7 is an exploded perspective view of the handpiece of FIG. 6.
Figure 8:
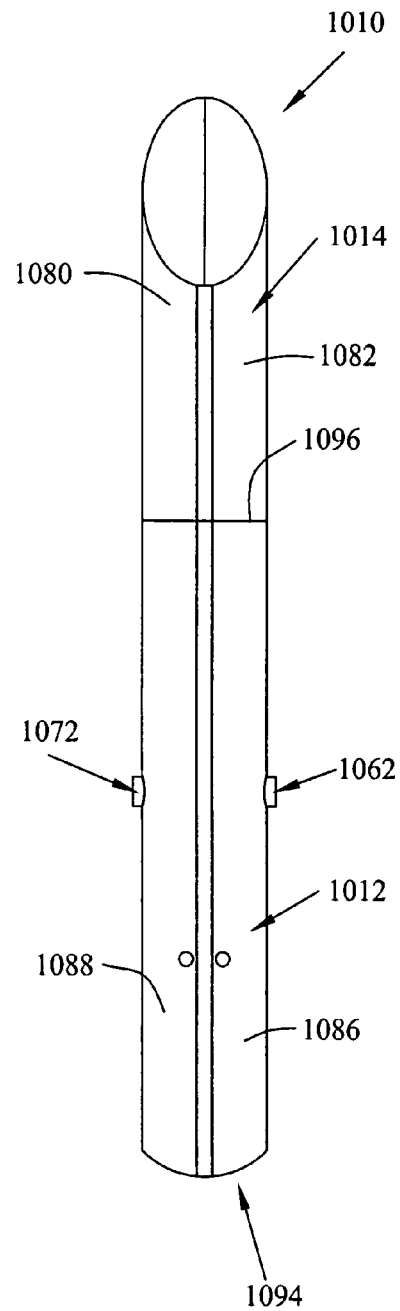
FIG. 8 is a rear elevational view of the handpiece of FIG. 6.
Figure 9:
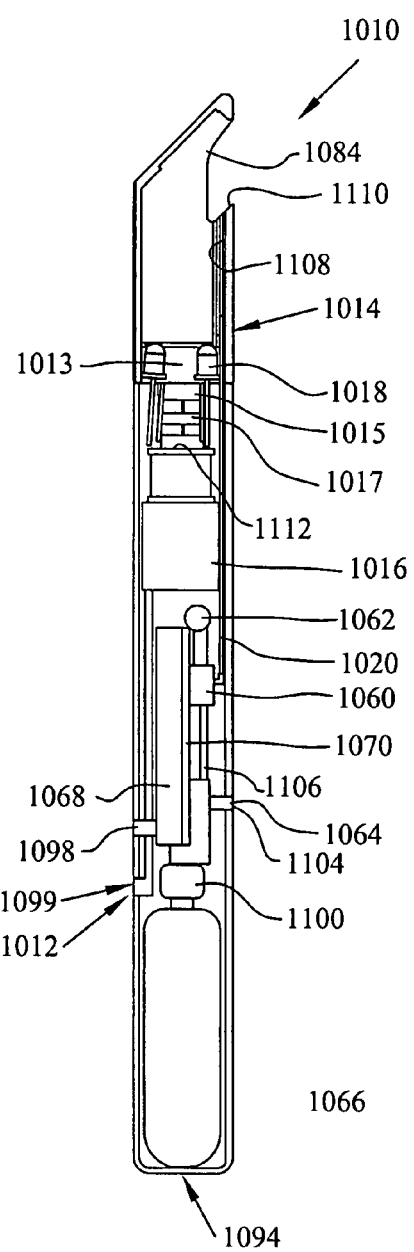
FIG. 9 is a side, partially cut-away, view of the handpiece of FIG. 6.
Figure 10:
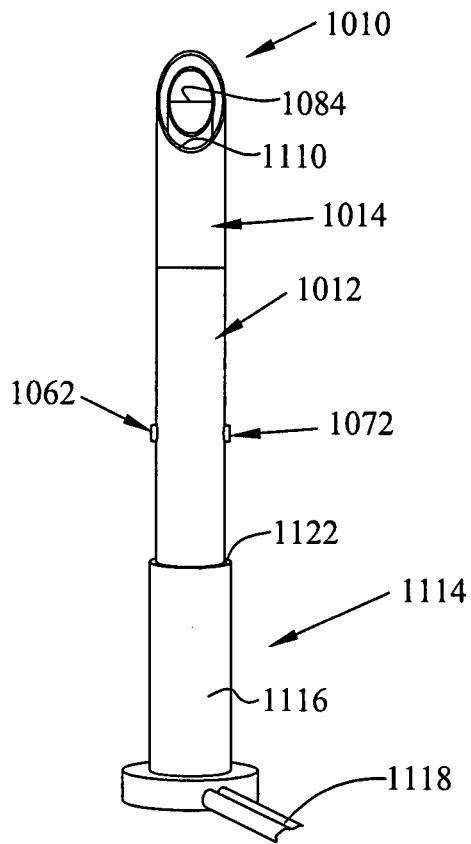
FIG. 10 is a perspective view of the handpiece of FIG. 6 in a cradle.

FIG. 5 shows a prior art handpiece 110 that is sold commercially by Inspektor. Inspektor handpiece 110 uses a detachable mirror 114 to aim light to tooth 54 and from tooth 54. Mirror 114 and mirror mount 115 detach such that mirror 114 and mirror mount 115 may be placed in an autoclave machine for purposes of sterilization. In use, Inspektor handpiece 110 is adjusted relative to tooth 54 such that the focal point 120 of a camera 116 is located on the tooth 54 surface. Maintaining the focal point 120 of camera 116 on the tooth 54 surface requires the provider to hold handpiece 110 steady. Proper placement of handpiece 110 is determined by using the received picture as feedback. In use, mirror 114 and a lens of camera 116 are open surfaces exposed to the oral environment. Thus, mirror 114 and lens of camera 116 are susceptible to collecting foreign debris.

Figure 12:
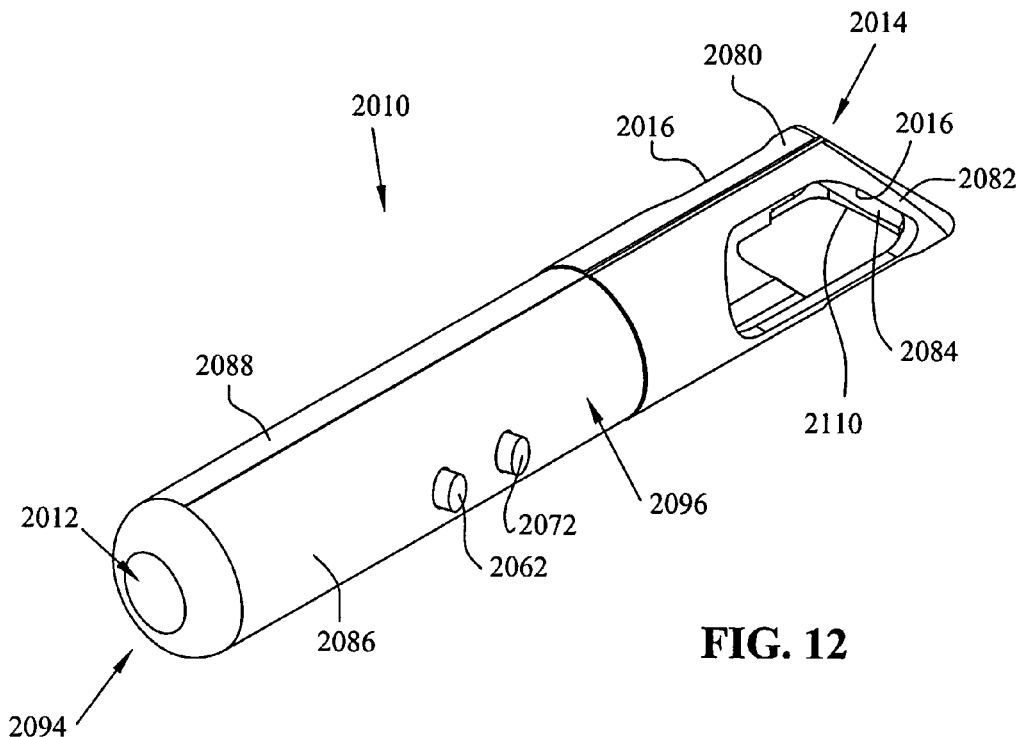
FIG. 12 is a perspective view of a third embodiment handpiece for detection of dental demineralization.
Figure 13:
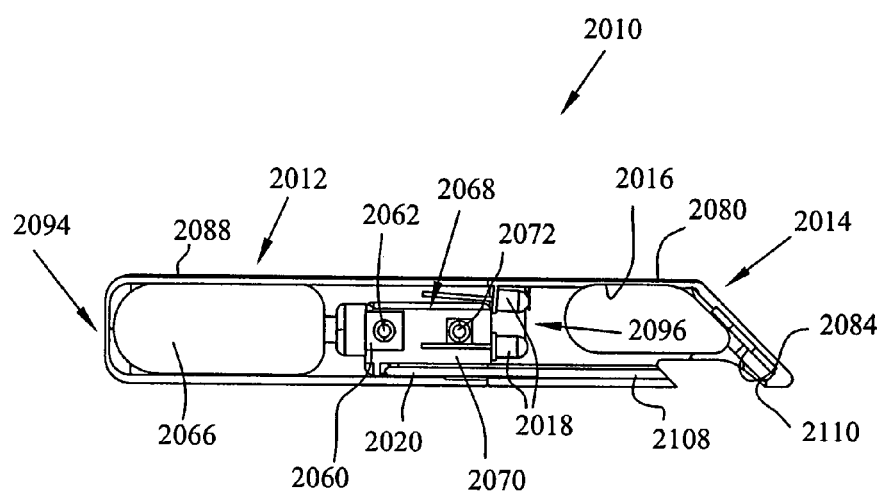
FIG. 13 is a side, partially cut-away, view of the handpiece of FIG. 12.
Figure 14:
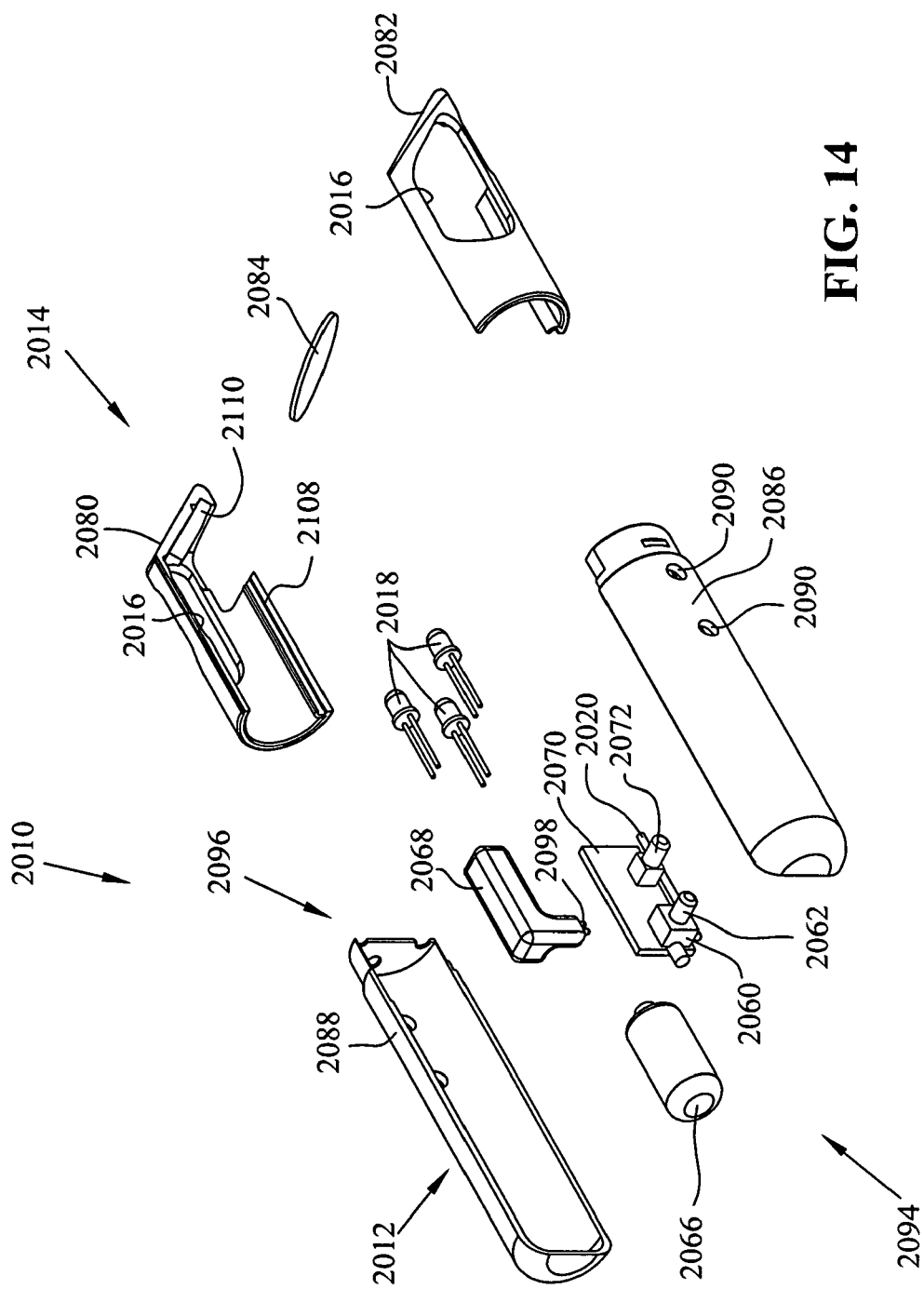
FIG. 14 is an exploded perspective view of the handpiece of FIG. 12.

Another embodiment handpiece 2010 is shown in FIGS. 12-14. Handpiece 2010 includes many similar pieces to those shown in handpiece 1010. Handpiece 2010 includes shell 2012 and end cap 2014 selectively attached to shell 2012. Shell 2012 houses LED's 2018, air outlet conduit 2020, air valve 2060 coupled to air outlet conduit 2020, air outlet valve button 2062, air canister 2066, battery 2068, electronics 2070, and LED activation button 2072.

Shell 2012 is composed from plastic, includes right shell housing 2086, and left shell housing 2088. Right shell housing 2086 includes two button holes 2090. Power lead holes (not shown) are also disposed within one or both of shell housings 2086, 2088. When assembled, right and left shell housings 2086, 2088 form a closed proximal end 2094 and an open distal end 2096. Open distal end 2096 includes an exterior groove therein (not shown) that cooperates with an inner surface (not shown) of end cap 2014 to provide a keyed interlock therebetween. Each button hole 2090 is sized shaped, and located to receive and allow external exposure of one of LED activation button 2072 and air outlet valve button 2062. Each power lead hole (not shown) is sized, shaped, and located to receive and allow external exposure of electrical leads 2098 of battery 2068.

End cap 2014 includes left end cap housing 2080, right end cap housing 2082, mirror 2084, and cap conduit 2108. Right and left end cap housings 2082, 2080 each include sight windows 2016 defined therein.

LED's 2018 emit light that reflects off mirror 2084 and illuminates tooth 54. In the current embodiment, LED's 2018 emit light having a wavelength of 405 nm.

Air canister 2066 couples to air valve 2060. While not shown, handpiece 2010 includes an air charging valve and related conduit, similar to air supply valve 1064. Air valve 2060 is operated via air outlet valve button 2062. Depression of air outlet valve button 2062 opens air valve 2060 and allows fluid communication between air canister 2066 and air outlet conduit 2020. Air outlet conduit 2020 fluidly couples to cap conduit 2108 when end cap 2014 is coupled to shell 2012. Air canister 2066 provides pressurized air in air valve 2060. Thus, depression of air outlet valve button 2062 allows the pressurized air to escape via air outlet conduit 2020 and cap conduit 2108. Valve 2060 may be electrically or mechanically operated and air outlet valve button 2062 may be an electrical or mechanical button. Depression of air outlet valve button 2062 allows valve 2060 to open for a pre-determined length of time. Alternatively, valve 2060 is opened as long as air outlet valve button 2062 is depressed.

As previously noted, battery 2068 includes exposed electrical leads 2098 that allow battery 2068 to be re-charged. One embodiment includes microphone (not shown) coupled to electronics 1070. Operation of the microphone is similar to operation of microphone 1099.

End cap 2014 selectively attaches to shell 2012 and includes excitation/air window 2110, cap conduit 2108, and sight windows 2016. End cap 2014 is designed to be disposable such that many disposable end caps 2014 would be used with each shell 2012 and its contents over the lifetime of handpiece 2010. Mirror 2084 is oriented at a 45 degree angle relative to tooth 54, although other angles may be used. Cap conduit 2108 is located such that air exiting therefrom creates a current along mirror 2084 and tooth 54. Sight windows 2016 provide clearance such that the dental care provider may view illuminated tooth 54 that is abutting air window 2110. A cradle (not shown), similar to cradle 1114, is also envisioned.

In use, a dental care provider selects handpiece 2010 and attaches end cap 2014 to shell 2012. The provider puts on goggles or glasses (not shown) having filters for lenses. The provider then places end cap 2014 portion of handpiece 2010 into the mouth of the patient such that air window 2110 of end cap 2014 abuts chosen tooth 54. LED's 2018 are activated via led activation button 2072 and the resulting fluorescence of tooth 54 is viewed by the dental care provider through sight windows 2016 and the glasses. When a suspected lesion is found, air outlet valve button 2062 is depressed to release air, and the change in fluorescence, if any, is viewed by the dental care provider. This allows the dental care provider to determine if the suspected lesion is an active lesion and appropriate measures may be taken.

Although the invention has been described in detail with reference to certain illustrated embodiments, variations exist within the scope and spirit of the invention as described and as defined in the following claims.

What is claimed is:

1. A handheld dental implement including:
   a housing defining an interior space;
   a power source;
   a light source electrically coupled to the power source;
   a light detecting device;
   a gas reservoir
   a mirror positioned to reflect light from the light source onto a diagnostic specimen and positioned to reflect light from the diagnostic specimen to the light detecting device; and
   a gas conduit positioned to transmit gas from the gas reservoir into contact with the mirror.

2. The implement of claim 1, further including a gas conduit having a first end and a second end, the first end being coupled to the gas reservoir and the second end being exposed to ambient air.

3. The implement of claim 2, further including a switch that selectively places the gas reservoir in fluid communication with ambient air.

4. The implement of claim 1, further including a gas input fluidly coupled to the gas reservoir.

5. The implement of claim 1, wherein the gas reservoir is rechargeable.

6. The implement of claim 1, wherein the light source is an LED.

7. The implement of claim 1, wherein the gas conduit is further positioned to transmit gas from the gas reservoir into contact with a diagnostic subject.

8. The implement of claim 1, wherein the light detecting device is coupled to the power source and coupled to an antenna.

9. The implement of claim 8, wherein the light detecting device and the antenna are both located within the interior space of the housing.

10. The implement of claim 1, further including a microphone coupled to the power source.

11. The implement of claim 1, further including a cradle including a bay sized and shaped to at least partially receive the housing therein.

12. The implement of claim 1, wherein the mirror is located on an interior portion of a removable end cap.

13. A handheld dental implement including:
    a power source;
    a light source electrically coupled to the power source;
    a microphone;
    an antenna coupled to the power source and the microphone;
    a light detecting device,
    a gas reservoir;
    a mirror positioned to reflect light from the light source onto a diagnostic specimen and positioned to reflect light from the diagnostic specimen to the light detecting device; and
    a gas conduit positioned to transmit gas from the gas reservoir into contact with the mirror.

14. The implement of claim 13, further including a housing defining an interior space.

15. The implement of claim 13, wherein the implement is wireless.

* * * * *